United States Patent [19]

Kaneta et al.

[11] Patent Number: 4,480,682
[45] Date of Patent: Nov. 6, 1984

[54] APPARATUS FOR FREEZING FERTILIZED OVA, SPERMATOZOA OR THE LIKE

[75] Inventors: Hiroshi Kaneta; Nobuo Sakao; Yasuo Kuraoka, all of Sapporo, Japan

[73] Assignee: Hoxan Corporation, Sapporo, Japan

[21] Appl. No.: 569,381

[22] Filed: Jan. 9, 1984

[30] Foreign Application Priority Data

Jan. 14, 1983 [JP] Japan .................................. 58-4738

[51] Int. Cl.³ ............................................ F25B 29/00
[52] U.S. Cl. ...................................... 165/14; 62/434; 62/467; 62/514 R
[58] Field of Search ................ 62/78, 62, 64, 96, 430, 62/514 R, 434, 467; 165/2, 32, 14

[56] References Cited

U.S. PATENT DOCUMENTS

| | | | |
|---|---|---|---|
| 4,030,314 | 6/1977 | Strehler et al. | 62/78 |
| 4,107,937 | 8/1978 | Chmiel | 62/78 |
| 4,117,881 | 10/1978 | Williams et al. | 62/78 |
| 4,232,453 | 11/1980 | Edelmann | 62/514 R |
| 4,314,450 | 2/1982 | Pelloux-Gervais | 62/78 |
| 4,314,459 | 2/1982 | Rivoire | 62/78 |
| 4,324,285 | 4/1982 | Henderson | 165/2 |
| 4,388,814 | 6/1983 | Schilling | 62/78 |

Primary Examiner—Ronald C. Capossela

Attorney, Agent, or Firm—George B. Oujevolk

[57] ABSTRACT

An apparatus for freezing fertilized ova, spermatozoa or the like has a heat transfer bottom board block formed at the lower end of a heat insulating peripheral wall with a lower refrigerant passage capable of flowing refrigerant. A bottom board temperature sensor is attached to the bottom board block, an upper heat transfer block is placed on the bottom board block through a heat insulating joint member, formed with an upper refrigerant passage for flowing the refrigerant. A temperature control heater, an upper block temperature sensor, a plurality of erecting tube charging spaces of tubes opened at the top thereof with the bottom board block as a bottom member are disposed between the peripheral wall and the upper block in such a manner that the tubes erected and charged into the spaces are cooled at the lower ends thereof by said bottom board block and at the upper part containing articles to be frozen such as fertilized ova, spermatozoa or the like are contained in buffer solution in said tubes. Thus, the buffer solutions in the tubes can be controlled to be cooled at the buffer solution of the lower noncontaining part by the bottom board block and the buffer solution of the containing part above the buffer solution of the lower noncontaining part by the upper block.

7 Claims, 4 Drawing Figures

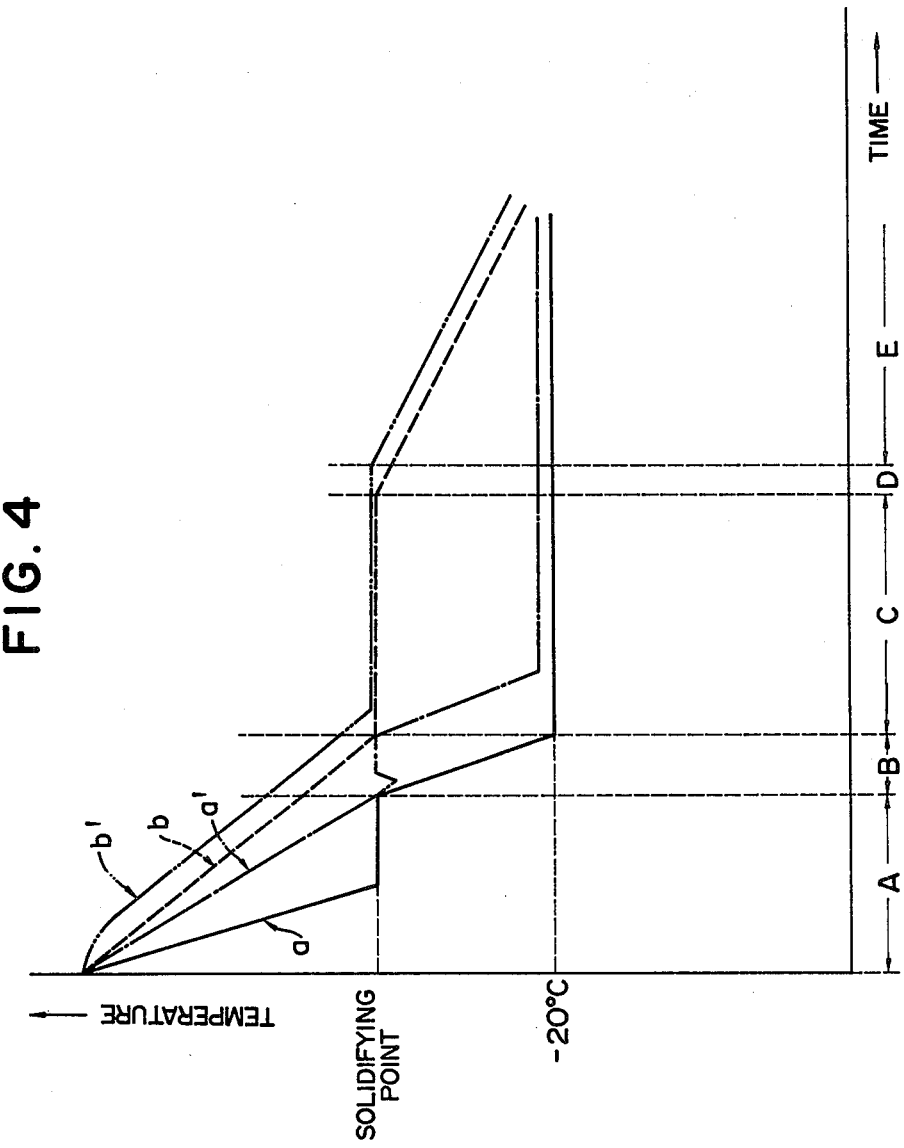

APPARATUS FOR FREEZING FERTILIZED OVA, SPERMATOZOA OR THE LIKE

BACKGROUND OF THE INVENTION

This invention relates to an apparatus for freezing fertilized ova, spermatozoa or the like.

Artificial fertilization has been recently frequently carried out to contrive the improvements of breed of domestic animal and of growth of the domestic animal. In this case, fertilized ova and spermatozoa have been preserved by freezing the same.

It is heretofore known to fill the fertilized ova and spermatozoa in a buffer solution contained in a tube and to freeze the buffer solution as a method of freezing the fertilized ova and spermatozoa.

A temperature change with respect to time of a pure substance when the substance is cooled under a constant pressure is generally known as a cooling curve. According to this principle, the substance does not always start to immediately freeze when the substance reaches its freezing point, but the substance will start generally freezing after the substance is overcooled to the temperature lower than its freezing point. Simultaneously, the substance raises its temperature to its true freezing point, and the substance will then lower its temperature again after the entire substance is completely frozen.

The buffer solution is overcooled at the freezing time in the freezing step according to the foregoing conventional freezing method which merely cools the substance. Then, the temperature of the substance or buffer solution is thereafter immediately raised. Therefore, the fertilized ova and spermatozoa are disadvantageously killed due to the thermal shock of this abrupt temperature change according to the conventional freezing method.

It has been proposed to avoid such a thermal shock in a method of freezing fertilized ova and spermatozoa to remove the buffer solution cooled to the freezing point and to hold a tube containing the buffer solution with a pincette preserved in liquefied nitrogen, thereby removing the freezing from the holding portion. This also lacks actual utilization due to the fact that the removal of the tube adversely affects the temperature of the buffer solution to fail in the freezing of the solution, so as and an automatic control is difficult due to the complicated operations.

Then, the present applicant has proposed a novel method, as disclosed in Japanese patent application No. 124,996/1981, of freezing fertilized ova, spermatozoa or the like comprising the steps of irregularly containing articles to be frozen such as fertilized ova, spermotozoa or the like in a buffer solution in a tube, cooling a buffer solution without the articles to be frozen with predetermined refrigerant so that the buffer solution without the articles to be frozen reaches a lower temperature than another buffer solution containing the articles to be frozen, thereby producing crystalline nuclei by freezing the buffer solution without articles to be frozen, and then cooling the crystalline nuclei so that the nuclei grow to the buffer solution containing the articles to be frozen to freeze the buffer solution containing the articles to be frozen, thereby freezing the article to be frozen such as fertilized ova, spermatozoa or the like.

More particularly, in this method, a buffer solution 2 is prepared by dissolving, for example, dimethyl sulfoxide (DMSO), dextrose, glycerin and/or sodium citrate in distilled water, the buffer solution 2 thus prepared is filled in a tube 1, e.g., a straw tube as shown in FIG. 1 or 2, and articles 3 to be frozen, e.g., fertilized ova, spermatozoa or the like are thrown into the buffer solution 2.

In this case, a cotton plug 4 or the like is charged in the lower end of the tube 1, and the articles 3 to be frozen are, on the other hand, floated in the middle of the buffer solution 2, or in this case the article 3 to be frozen is contained an irregular position at the lower half portion of the buffer solution 2, in which case segmenting gaps 5 may sometimes be formed with air bubbles at a certain position or positions or the buffer solution 2 as shown in FIG. 2.

When the above tube 1 is then cooled, the tube 1 is not cooled, but the difference of phases is provided at the cooling temperature between a buffer solution segment $2a$ containing the fertilized ova, spermatozoa or the like as the articles 3 to be frozen in the middle portion of the tube 1 and a buffer solution segment $2b$ containing no article 3 in the lower portion of the tube 1, the buffer solution segment $2b$ is first frozen to form crystalline nuclei, and the crystalline nuclei thus produced are then grown to the buffer solution segment $2a$, thereby freezing the articles 3, e.g., the fertilized ova, spermatozoa or the like.

OBJECTS OF THE INVENTION

Accordingly, a primary object of this invention is to provide an apparatus for freezing fertilized ova, spermatozoa or the like which can be used to carry out the above-described method, can be readily handled by eliminating complicated operations such as cooling the tube 1 by dipping the tube directly in a refrigerant such as an $LN_2$ and removal of the tube, can easily control the temperature thereof and can effectively avoid killing the fertilized ova, spermatozoa or the like due to abrupt temperature rise.

The above and other related objects and features of the invention will be apparent from a reading of the following description of the disclosure found in together with the accompanying drawings and the novelty thereof pointed out in the appended claims.

BRIEF DESCRIPTION OF THE DRAWINGS

FIG. 4 is a graph showing the temperature controlling steps of respective sections to illustrating the operating states of the apparatus.

DESCRIPTION OF THE PREFERRED EMBODIMENTS

The present invention will now be described in more detail with reference to the accompanying drawings.

Figure 1:
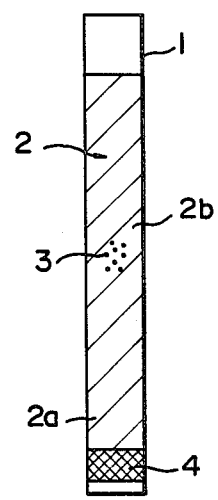
FIG. 1 is a front, longitudinally sectional explanatory view of a tube containing fertilized ova, spermatozoa or the like of the prior art.
Figure 2:
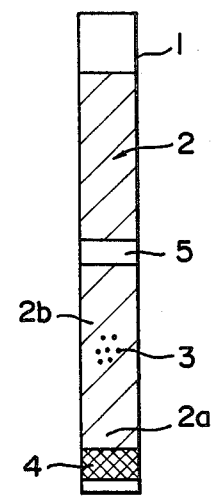
FIG. 2 is a front, longitudinally sectional explanatory view of a tube containing fertilized ova, spermatozoa or the like of another prior art device.
Figure 3:
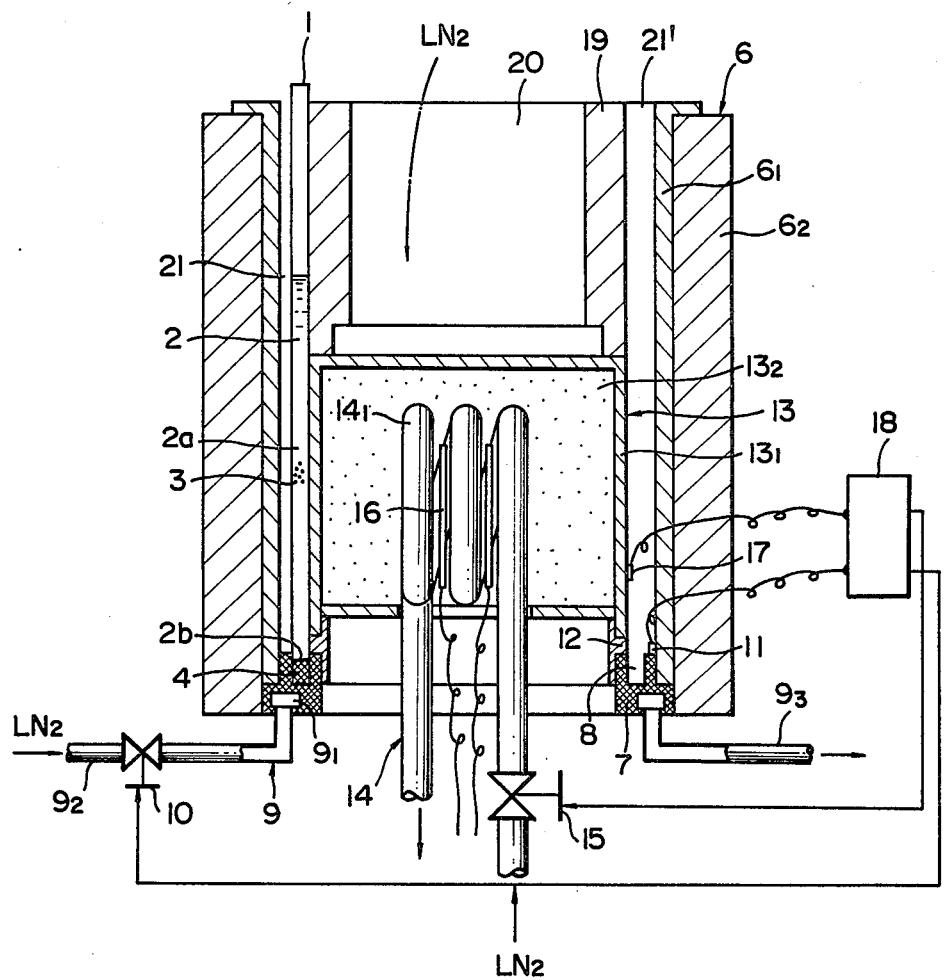
FIG. 3 is a front, longitudinally sectional explanatory view of an apparatus for freezing fertilized ova, spermatozoa or the like constructed according to the present invention.

Referring to FIG. 3, which shows a preferred embodiment of an apparatus for freezing fertilized ova, spermatozoa or the like according to the present invention, wherein like reference numerals designate the same or equivalent parts in FIGS. 1 and 2, a heat insulating materials $6_1$ is provided on the outside of a peripheral wall $6_1$ such as a Teflon (trademark) or an FRP to construct a heat insulating peripheral wall 6, and an annular heat transfer bottom board block 7 is fixedly secured by such means as an internal bonding or the like to the lower end of the inner periphery of the peripheral wall 6.

The bottom board block 7 is formed of copper. A heat transfer recess 8 such as a hole or a peripheral groove is formed to be engaged with the lower end of the tube 1, to be described later, on the upper surface of the bottom board block 7. A lower refrigerant passage 9 is of a refrigerant cavity $9_1$ formed in the bottom board block 7, an inflow pipe $9_2$ connected to the cavity $9_1$ and an outflow pipe $9_3$ connected to the cavity 9. A control valve 10 is provided at the inflow pipe $9_2$ for opening and closing the pipe. When the control valve 10 is opened, the refrigerant such as $LN_2$ is passed through the passage 9. A bottom board temperature sensor 10 is provided to detect the temperature of the bottom board block 7 cooled by the refrigerant.

An upper heat transfer block 13 is laid on the top of the bottom board block 7 through a heat insulating joint member 12 of ring shape made of an FRP. The upper block 13 shown in FIG. 3 is constructed to fill a copper mesh unit $13_2$ in a copper outer shell $13_1$ in such a manner that an upper refrigerant passage 14 formed with a heat exchange unit $14_1$, in which a coiled metal pipe is mounted, is buried in the mesh unit $13_2$. A control valve 15 is provided at a guide passage $14_1$ extended externally of the passage 14. When the control valve 15 is opened, the refrigerant such as $LN_2$ is flowed through the passage 14. A temperature control heater 16 is attached to the heat exchange unit $14_1$ for controlling the current to the heater 16, thereby regulating the temperature of the upper block 7 cooled by the $LN_2$. Further, in order to obtain the temperature of the block 7, an upper block temperature sensor 17 is provided in the vicinity of the lower portion in contact with the surface at the outer shell $13_1$.

Reference numeral 18 designates a controller capable of performing a calculation, which receives input signals from the temperature sensor 10 and the temperature sensor 17, and produces an output signal to control to open or close the valves 10 and 15. Further, there is also provided a cooling tank 20 which is formed of a wall 19 laid on the top of the upper block 7 and the upper block 7, to which tank the refrigerant such as $LN_2$ can be filled as required. When the $LN_2$ is filled in the tank 20, the tubes 1, 1, . . . which are filled with frozen fertilized ova therein, can be dipped and stored.

With the structure thus constructed described above, erecting tube charging spaces 21 of the erected tube opened at the top are formed with the bottom board block 7 used as a bottom member. When the aforementioned tubes 1, 1, . . . shown in FIGS. 1 and 2 are respectively inserted into the tube charging spaces 21 are erected, the lower ends of the tubes 1, 1, . . . charged into the heat transfer recess 8 is cooled by the bottom board block 7 and the upper parts above the lower ends of the tubes 1, 1, . . . are cooled by the upper block 13. In the embodiment shown in FIG. 3, the spaces 21 are opened as a hole 21' between the peripheral wall $6_1$ and the wall 19 formed in the same diameter as the upper block 13

In order to, then, freeze the fertilized ova, spermatozoa or the like with the foregoing apparatus of the construction described, the tubes 1, 1, . . . are respectively charged into the charging spaces 21, the valves 10 and 15 are opened by the controller 18, the heater 16 is controlled to heat the bottom board block 7 and the upper block 13 to a predetermined temperature. Thus, as shown by the first time zone A in FIG. 4, the bottom board block 7 is cooled, as designated by a solid line curve a in FIG. 4, to the solidifying temperature of the buffer solutions 2 contained in the tubes 1, 1, . . . and the solidifying point is maintained.

The upper block 13 is simultaneously cooled, as designated by a solid line curve b in FIG. 4, by the $LN_2$ and the heater 16 to be controlled so that the cooling temperature becomes a level higher by approx. 5° C. than the solidifying point at the final time point in the first time zone A of the bottom board block 7.

The bottom board block 7 which is thus maintained at the solidifying temperature is then further cooled to a level lower by $-20°$ C. than the solidifying temperature, in which case the upper block 13 is cooled continuously to the solidifying point when it reaches $-20°$ C. in the second time zone B.

When the bottom board block 7 is controlled to be cooled as described, the buffer solution of the boundary in contact with a plug 4 of the tube 1 placed on the block 7 is cooled, as designated by a dotted-broken line curve a' in FIG. 4, and the buffer solution of this part is partly overcooled to cause nuclei of the crystal to be produced, and the crystal is thereafter grown toward the upward direction in the second time zone B.

In the third time zone C, the buffer solution 2 in the tube 1 is all frozen. Thus, the bottom board block 7 and the upper block 13 are controlled to be maintained in a constant temperature state. Further, in the fourth time zone D and fifth time zone E, only the upper block 13 is cooled, as shown in FIG. 4, to the final freezing temperature. With a series of cooling controls as described, the buffer solution in the vicinity of frozen state is cooled out of phase, as designated by two-dotted broken line b', from the cooling state b of the upper block 13. Consequently, no overcooling phenomenon occurs, and the articles 3 which are to be frozen can be frozen.

Since the apparatus for freezing fertilized ova, spermatozoa or the like of the invention is constructed to comprise a heat transfer bottom board block 7 formed at the lower end of a heat insulating peripheral wall 6 with a lower refrigerant passage 9 capable of flowing refrigerant, a bottom board temperature sensor 11 attached to said bottom board block, an upper heat transfer block 13 placed on said bottom board block through a heat insulating joint member, formed with an upper refrigerant passage 14 for flowing the refrigerant, a temperature control heater 16, an upper block temperature sensor 17, a plurality of erecting tube charging spaces 21 of tubes opened at the top thereof with the bottom board block 7 as a bottom member between said peripheral wall 6 and said upper block 13 in such a manner that the tubes 1, 1, . . . respectively erected and charged into the spaces 21 are cooled at the lower ends thereof by said bottom board block 7 and at the upper part containing articles 3 to be frozen such as fertilized ova, spermatozoa or the are like contained in buffer solution in said tubes, the buffer solutions 2 in the tubes 1 can be controlled to be cooled at the buffer solution $2b$ of the lower noncontaining part by said bottom board block 7 and the buffer solution $2a$ of the containing part above the buffer solution $2b$ of the lower noncontaining part by said upper block 13. Thus, nuclei of crystal is produced in the buffer solution $2b$, then grown in the buffer solution 2a of the containing part, thereby eliminating the action of the abrupt temperature rise due to overcooling when the fertilized ova, spermatozoa or the like is frozen. Consequently, the killing of the fertilized ova, spermatozoa or the like can be avoided, thereby obtaining the freezing of the fertilized ova, spermatozoa or the like having high content of survival rate.

Since the tubes 1, 1, . . . are not dipped in liquid nitrogen, the handling of the apparatus of the invention can be simple and the temperature control can be readily automated.

What is claimed is:

1. An apparatus for freezing fertilized ova, spermatozoa or the like comprising:
    a heat transfer bottom board block formed at the lower end of a heat insulating peripheral wall with a lower refrigerant passage capable of flowing refrigerant,
    a bottom board temperature sensor attached to said bottom board block for detecting the temperature of said bottom board block,
    an upper heat transfer block placed on said bottom board block through a heat insulating joint member, formed with an upper refrigerant passage for flowing the refrigerant,
    a temperature control heater,
    an upper block temperature sensor, and
    a plurality of erecting tube charging spaces of tubes opened at the top thereof with the bottom board block as a bottom member between said peripheral wall and said upper block in such a manner that the tubes respectively erected and charged into the spaces are cooled at the lower ends thereof by said bottom board block and at the upper part containing articles to be frozen such as fertilized ova, spermatozoa or the like contained in buffer solution in said tubes.

2. The apparatus as claimed in claim 1, wherein said heat transfer bottom board block is annularly fixedly secured by an internal bonding to the lower end of the inner periphery of the peripheral wall and made of copper.

3. The apparatus as claimed in claim 1, wherein a lower refrigerant passage is formed of a refrigerant cavity formed in said bottom board block, an inflow pipe connected to the cavity and an outflow pipe connected to the cavity, and a control valve provided at the inflow pipe for opening and closing the pipe.

4. The apparatus as claimed in claim 1, wherein said upper heat transfer block is constructed to fill a copper mesh unit in a copper outer shell in such a manner that an upper refrigerant passage formed with a heat exchange unit, in which a coiled metal pipe is mounted, is buried in the mesh unit.

5. The apparatus as claimed in claim 4, wherein said temperature control heater is attached to the heat exchange unit for controlling a current to said temperature control heater to regulate the temperature of the upper heat transfer block.

6. The apparatus as claimed in claim 4, wherein said upper block temperature sensor is provided in the vicinity of the lower portion thereof in contact with the surface of the outer shell.

7. The apparatus as claimed in claim 6, wherein a controller is provided to receive input signals from said bottom board temperature sensor and said upper block temperature sensor and to produce an output signal to control for opening or closing said control valve provided at the inflow pipe and said control valve provided at a guide passage extended externally of said upper refrigerant passage.

* * * * *